United States Patent [19]

White

[11] 4,341,777
[45] Jul. 27, 1982

[54] CEPHALOSPORIN ANTIBIOTIC

[75] Inventor: Herbert J. White, Chalfont St. Giles, England

[73] Assignee: Glaxo Group Limited, London, England

[21] Appl. No.: 184,383

[22] Filed: Sep. 5, 1980

[30] Foreign Application Priority Data

Sep. 10, 1979 [GB] United Kingdom ................ 7931379

[51] Int. Cl.³ .................. A61K 31/545; C07D 501/34
[52] U.S. Cl. ........................................ 424/246; 544/28
[58] Field of Search ........................... 544/28; 424/246

[56] References Cited

U.S. PATENT DOCUMENTS 3,971,778  7/1976  Cook et al. ........................... 544/28
3,974,153  8/1976  Cook et al. ........................... 544/22

Primary Examiner—Paul M. Coughlan, Jr.
Attorney, Agent, or Firm—Bacon & Thomas

[57] ABSTRACT

A substantially non-hygroscopic sodium salt of (6R,7R)-3-acetoxymethyl-7-[(Z)-2-(fur-2-yl)-2-methoxyiminoacetamido]ceph-3-em-4-carboxylic acid. The salt is crystalline and may be prepared by crystallization from an ethanolic solvent medium containing not greater than about 6% by volume of water. The salt exhibits antibiotic properties and may be formulated in pharmaceutical compositions for human or veterinary medicine.

12 Claims, 1 Drawing Figure

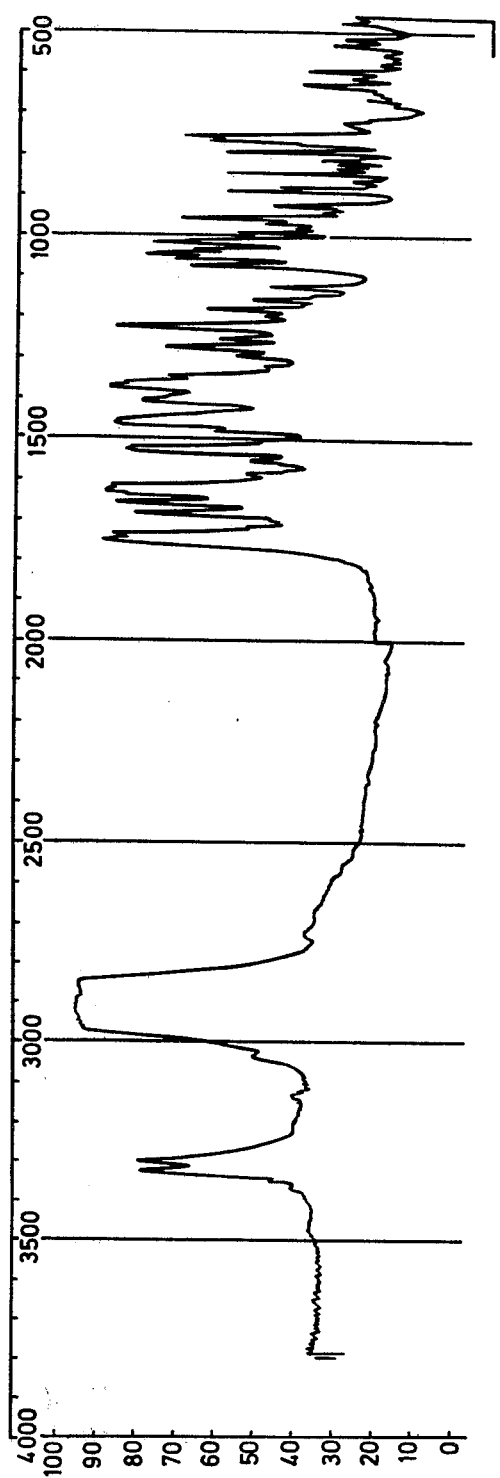

CEPHALOSPORIN ANTIBIOTIC

The present invention is concerned with improvements in or relating to the production and isolation of the sodium salt of (6R,7R)-3-acetoxymethyl-7-[(Z)-2-(fur-2-yl)-2-methoxyiminoacetamido]ceph-3-em-4-carboxylic acid.

(6R,7R)-3-Acetoxymethyl-7-[(Z)-2-(fur-2-yl)-2-methoxyiminoacetamido]ceph-3-em-4-carboxylic acid possesses anti-bacterial activity against a range of gram-positive and gram-negative organisms coupled with particularly high stability to β-lactamases produced by various gram-negative organisms and can be used as a broad spectrum antibiotic.

Moreover, (6R,7R)-3-acetoxymethyl-7-[(Z)-2-(fur-2-yl)-2-methoxyiminoacetamido]ceph-3-em-4-carboxylic acid is an important intermediate in the production of other cephalosporin antibiotics having the 7-[(Z)-2-(fur-2-yl)-2-methoxyiminoacetamido]-side chain. One such antibiotic which is of commercial importance is cefuroxime which is described in British Pat. No. 1,453,049.

The preparation of the above-mentioned 3-acetoxymethyl cephalosporin compound is described, for example, in British Pat. No. 1,399,086, the process essentially involving the acylation of (6R,7R)-7-aminocephalosporanic acid with (Z)-2-(fur-2-yl)-2-methoxyiminoacetyl chloride. The cephalosporin compound may be recovered in the form of a sodium salt which exhibits the interesting pharmacological activity mentioned above. The sodium salt is of particular importance since it facilitates formulation in pharmaceutical compositions.

The sodium salt has previously only been obtained in a hygroscopic form (referred to herein as Form B) by treatment of solutions of the free acid in wet ethyl acetate with a solution of sodium 2-ethylhexanoate in the same solvent. The Form B sodium salt thus obtained contains about 4% mole/mole (m/m) of water at normal atmospheric humidity (approximately 45% relative humidity); the water content increases to over 15% m/m at 83% relative humidity. Thus, Form B of the sodium salt is somewhat unsuitable for use as a pharmaceutical product as the water content varies considerably depending on the ambient humidity and it is difficult to obtain a consistent pharmaceutical product.

We have now discovered that (6R,7R)-3-acetoxymethyl-7-[(Z)-2-(fur-2-yl)-2-methoxyiminoacetamido]-ceph-3-em-4-carboxylic acid can be advantageously prepared and isolated in the form of a substantially non-hygroscopic sodium salt, and such a salt constitutes one feature of this invention.

This non-hygroscopic sodium salt is designated as Form A, and has been found to be more highly crystalline than the hitherto known Form B which does not appear to exist in a true crystalline form. The Form A sodium salt contains less than 1% m/m of water and we have found it to be non-hygroscopic at relative humidities within the range 25-83%. We have now established that Form A has a greater long-term stability than Form B and because of this and its low hygroscopicity, it is far more suitable for use in pharmaceutical compositions.

The precise conditions under which Form A sodium salt is formed may be empirically determined and a number of methods have been found, as a matter of practice, to be suitable.

In another aspect, the invention also provides a process for the preparation of the Form A sodium salt, which process comprises crystallising the said salt from a solution of a sodium salt of (6R,7R)-3-acetoxymethyl-[(Z)-2-(fur-2-yl)-2-methoxyiminoacetamido]-ceph-3-em-4-carboxylic acid or a solvate thereof in an ethanolic solvent medium containing not greater than about 6% by volume of water.

Thus, for example, this non-hygroscopic form of the sodium salt may be prepared by crystallisation under controlled conditions. In particular, the Form A sodium salt can be prepared from the corresponding acid or by recrystallisation of a previously isolated sodium salt or solvate thereof.

When the starting material for the preparation of the desired Form A sodium salt is the corresponding acid, a preferred procedure of preparation involves treating a solution of the acid in an organic solvent, such as industrial methylated spirit (that is, a mixture containing not less than 95% by volume of ethanol, 3.5 to 5% by volume of methanol and not more than 1% by volume of water) or wet ethyl acetate, with a solution of a sodium salt of an organic acid, such as sodium 2-ethylhexanoate, in industrial methylated spirit, whereby the desired Form A sodium salt crystallises directly. Alternatively, the solution of the starting acid may be extracted into an aqueous solution of a sodium salt of a weak organic acid, such as, for example, acetic acid, conveniently a small volume, followed by dilution of the aqueous extract with industrial methylated spirit until the water content of the final solution is not greater than about 6% by volume of water, whereupon the Form A salt crystallises. Other sodium salts of organic acids which may be used in these preparative techniques include, for example, the sodium salt of lactic and hexanoic acids.

When the starting material for the preparation of the desired Form A sodium salt is Form B sodium salt or a solvate thereof, a preferred procedure of preparation involves diluting a concentrated (e.g. 30–40% m/m) solution of the starting sodium salt in an aqueous industrial methylated spirit containing 25 to 50% by volume of water with industrial methylated spirit containing not more than 1% by volume of water until the water concentration is not greater than about 6% by volume, the desired Form A sodium salt thereby crystallising. The aqueous industrial methylated spirit used to dissolve the starting material may be replaced by methanol.

The Form A sodium salt may further be conveniently prepared from Form B sodium salt or solvate thereof by crystallisation from industrial methylated spirit containing up to about 6% by volume of water, the sodium salt generally being insufficiently soluble at lower water contents and the yield of the desired Form A salt decreasing rapidly at water contents above about 6% by volume.

Form A sodium salt may also be prepared by slurrying Form B sodium salt or a solvate thereof with industrial methylated spirit under conditions whereby the desired Form A salt crystallises.

If desired, the Form A sodium salt prepared by any one of the above described methods may further be recrystallised e.g. by similar methods to those mentioned above for the preparation of the Form A salt from Form B sodium salt.

Form A sodium salt may also be conveniently prepared from a solvate of sodium (6R,7R)-3-acetoxymethyl-7-[(Z)-2-(fur-2-yl)-methoxyiminoacetamido]ceph-3-em-4-carboxylate, for example, the dioxan solvate, by the methods described herein.

As indicated above, the non-hygroscopic Form A sodium salt of the invention may be used as a broad spectrum antibiotic and may thus be formulated for administration in any convenient way, by analogy with other antibiotics. The invention therefore includes within its scope pharmaceutical compositions comprising the substantially non-hygroscopic Form A sodium salt of (6R,7R)-3-acetoxymethyl-7-[(Z)-2-(fur-2-yl)-2-methoxyiminoacetamido]ceph-3-em-4-carboxylic acid adapted for use in human or veterinary medicine. Such compositions may be presented for use in conventional manner with the aid of any necessary pharmaceutical or veterinary carriers or excipients.

The Form A sodium salt may be formulated for injection and may be presented in unit dose form in ampoules or in multi-dose containers, if necessary with an added preservative. The compositions may also be in the form of suspensions, solutions or emulsions in oily or aqueous vehicles, and may contain formulatory agents such as suspending, stabilising and/or dispersing agents. Alternatively the active ingredient may be in powder form for reconstitution with a suitable vehicle, e.g. sterile, pyrogen-free water, before use.

The compositions may also be formulated as suppositories, e.g. containing conventional suppository bases such as cocoa butter or other glycerides.

The compound of the invention may be administered in combination with other compatible therapeutic agents such as other antibiotics, e.g. penicillins, cephalosporins and tetracyclines.

Compositions for use in veterinary medicine may for example, be formulated as intramammary injections in either long acting or quick-release bases.

If desired, intramammary injections may contain other active ingredients e.g. a corticosteroid, or another antibiotic e.g. a cephalosporin or penicillin.

Intramammary preparations may be sterile solutions or suspensions in aqueous or oily vehicles, but in order to obtain products with a suitable shelf life, they are generally formulated as suspensions in oily vehicles. Such products may be manufactured aseptically by dispersing the sterile active ingredient(s) in the oily vehicle which has previously been sterilised by heat or possibly by filtration. The active ingredient(s) itself may have been manufactured aseptically or sterilised after manufacture by methods such as gamma irradiation or exposure to ethylene oxide. Any heat-labile constituent of the product may be sterilised by these methods. The final product may if desired be presented in unit dose collapsible metal tubes or plastic syringes, with a smooth tapered nozzle to facilitate insertion into the teat canal.

Oils used in intramammary injection vehicles may be mineral oils (such as liquid paraffin) or vegetable oils (such as arachis oil or cottonseed oil). Alternatively, triglycerides or propylene glycol diesters of saturated fatty acids derived from vegetable oils may be used. The oils may contain a thickening or suspending agent such as soft or hard paraffins, beeswax, 12-hydroxy stearin, hydrogenated arachis oil, aluminium stearates or glyceryl monostearate. Where the products are employed in lactating animals, it is desirable for the vehicle and medicament to disperse rapidly in the mammary tissue and to be excreted rapidly in the milk. To assist in achieving this, hydrophilic materials such as polyethylene glycols or non-ionic surfactants such as polysorbate 60, sorbitan monostearate, glyceryl monostearate or cetomacrogol 1000 may be incorporated. Intramammary injections may also contain a tracer substance such as the dye, brilliant blue FCF. Other constituents may include stabilisers (such as procaine), antioxidants (e.g. gallates) or preservatives (e.g. chlorocresol).

When the veterinary compositions are formulated for parenteral injection they are generally in the form of sterile solutions or, more probably, as suspensions in an oily vehicle, and the above mentioned vegetable oils, triglycerides or ethyl oleate are suitable for this purpose. In general, the product viscosity should be low to facilitate passage through an injection needle but suspending agents such as aluminium stearate or glyceryl monostearate may be desired. Such a product may be presented in a multi-dose container, if necessary with an added preservative.

In general the compositions may contain from 0.1% upwards, e.g. 0.1 to 99%, preferably from 2 to 60% of the active material, depending on the method of administration. Where the compositions comprise dosage units, each unit will preferably contain 50 to 1500 mg of the active ingredient. The compositions formulated for intramammary injection will preferably contain 100 to 300 mg of the active ingredient, e.g. 150 to 200 mg. The dosage as employed for adult human treatment will preferably range from 500 to 4000 mg per day, depending on the route and frequency of administration.

The following Preparations and Examples together serve to illustrate the preparation of the Form A sodium salt according to the invention and pharmaceutical and veterinary compositions containing it. In the Preparations and Examples, all temperatures are in °C.

PREPARATION 1

A solution of (6R,7R)-7-[(Z)-2-(fur-2-yl)-2-methoxyiminoacetamido]ceph-3-em-4-carboxylic acid was prepared by acylation of (6R,7R)-7-amino cephalosporanic acid toluene-4-sulphonate dihydrate (19.0 g) with (Z)-2-(fur-2-yl)-2-methoxyiminoacetyl chloride in a mixture of dichloromethane (120 ml) and N,N-dimethylacetamide (30 ml). Water (150 ml) was added and the mixture stirred for 5 minutes at 20° to 25°. The aqueous phase was separated and the organic phase washed again with water (150 ml). The aqueous washes were sequentially extracted with fresh dichloromethane (25 ml) and the latter bulked with the main organic phase. The bulked organic phases were concentrated in vacuo, industrial methylated spirit (50 ml) was added, and concentration continued to a residual volume of 50 ml. The concentrate was stirred while a solution of sodium 2-ethylhexanoate (10 g) in industrial methylated spirit (40 ml) was added, followed immediately by dioxan (10 ml). The stirrer was then stopped and crystallisation allowed to proceed from the static solution. After 2 hours the crystalline solid was filtered, washed with 10% v/v dioxan in industrial methylated spirit (2×25 ml), and dried in vacuo, to yield sodium (6R,7R)-7-[(Z)-2-(fur-2-yl)-2-methoxyimino-acetamido]ceph-3-em-4-carboxylate, dioxan solvate (18.2. g). $[\alpha]_D + 56.7°$.

The isolated product was shown by gas liquid chromatography assay to contain 15% w/w of dioxan.

PREPARATION 2

A solution of (6R,7R)-7-[(Z)-2-(fur-2-yl)-2-methoxyiminoacetamido]ceph-3-em-4-carboxylic acid (ca. 42 g) prepared in wet ethyl acetate (ca. 1.7% $H_2O$) (545 ml) was stirred and a solution of sodium 2-ethylhexanoate (18.3 g) in ethyl acetate (180 ml) was added. The solution was stirred for 30 minutes to give a thick suspension. The product was isolated by filtration, washed with ethyl acetate (4×50 ml) and dried at 40° in vacuo to give the desired Form B sodium salt containing 4.4% m/m of water (by Karl Fischer) (35.4 g).

A sample of the Form B sodium salt containing 3.9% m/m of water (Karl Fischer) prepared by the above method was subsequently subjected to Debye Scherrer powder X-ray diffraction. The sample of the Form B salt in 0.3 mm diameter capillaries was photographed in a 114.6 mm diameter powder diffraction camera using Co Kα radiation. The line intensities were compared against a set of standards and converted to the relative intensities shown in the following Table I:

TABLE I

| 'd' value (Å) | Relative intensity (I/I$_{100}$) |
|---|---|
| 10.1 | 100 |
| 8.27 | 11 |
| 6.92 | 33 |
| 6.56 | 22 |
| 5.11 | 17 |
| 4.82 | 39 |
| 4.58 | 22 |
| 4.47 | 67 |
| 4.14 | 22 |
| 3.96 | 17 |
| 3.85 | 11 |
| 3.77 | 22 |
| 3.58 | 39 |
| 3.38 | 6 |
| 3.30 | 1 |
| 3.20 | 3 |
| 3.18 | 1 |
| 3.04 | 2 |
| 2.94 | 2 |
| 2.80 | 2 |
| 2.73 | 6 |
| 2.18 | 2 |
| 2.09 | 17 |

EXAMPLE 1

A solution of (6R,7R)-7-[(Z)-2-(fur-2-yl)-2-methoxyiminoacetamido]ceph-3-em-4-carboxylic acid (ca. 21 g) prepared in ethyl acetate (150 ml) was extracted with a solution of anhydrous sodium acetate (6 g) in water (22 ml) to give an aqueous layer containing the sodium salt of the cephalosporin. This clear aqueous solution was separated off and added to industrial methylated spirit (95% ethanol) (600 ml) and the clear solution was seeded and stirred at ambient temperature for 30 minutes. The resulting suspension was stored at 0° for 20 hours and the crystalline product was then collected by filtration, washed with industrial methylated spirit (4×30 ml) and dried at 40° in vacuo for 5 hours to produce the required Form A sodium salt (14.52 g).

| | |
|---|---|
| Impurities (by thin layer chromatography) | 1.0% |
| Impurities (by high performance liquid chromatography) | 2.7% |
| Water (by Karl Fischer) | 0.3% |
| Solvents (by GLC) | 0.25% (ethanol) |
| [α]$_D$(1% in H$_2$O) | +66° |
| E$_{1cm}^{1\%}$ in pH 7.0 buffer at 274 nm | 411 |
| Sulphated ash | 15.8% m/m |

X-Ray Diffraction

The product of this Example was stored at 2° C. for 24 hours prior to being X-rayed in 0.3 mm diameter capillaries. A Debye Scherrer powder diffraction photograph was then prepared in a 114.6 mm diameter camera using Co Kα radiation.

The line intensities were compared against a set of standards and converted to the relative intensities shown in the following Table II:

TABLE II

| 'd' Value (Å) | Relative Intensity (I/I$_{100}$) |
|---|---|
| 14.4 | 55 |
| 12.3 | 100 |
| 9.9 | 45 |
| 7.16 | 36 |
| 6.79 | 64 |
| 6.59 | 73 |
| 6.35 | 9 |
| 6.11 | 5 |
| 4.92 | 27 |
| 4.69 | 100 |
| 4.49 | 41 |
| 4.20 | 9 |
| 4.00 | 45 |
| 3.91 | 36 |
| 3.78 | 36 |
| 3.64 | 90 |
| 3.55 | 36 |
| 3.36 | 18 |
| 3.30 | 27 |
| 3.25 | 9 |
| 3.16 | 18 |
| 3.08 | 27 |
| 2.86 | 18 |
| 2.81 | 18 |
| 2.76 | 14 |
| 2.60 | 14 |
| 2.56 | 4 |
| 2.45 | 18 |
| 2.42 | 14 |
| 2.36 | 4 |
| 2.31 | 18 |
| 2.262 | 14 |
| 2.188 | 23 |
| 2.054 | 9 |
| 2.025 | 4 |
| 2.000 | 4 |
| 1.915 | 4 |
| 1.800 | 2 |
| 1.728 | 2 |

It will be noted that these figures differ substantially from those given above for the product of Preparation 2 (Form B).

Infrared Spectrum

The infrared spectrum of the product of this Example as a Nujol mull was obtained and this is shown in the Figure of the accompanying drawing. This spectrum is used as a reference for the products of the following Examples.

EXAMPLE 2

A solution of (6R,7R)-3-acetoxymethyl-7-[(Z)-2-(fur-2-yl)-2-methoxyiminoacetamido]ceph-3-em-4-carboxylic acid (ca. 22 g) prepared in ethyl acetate (200 ml) containing 2.3% water was stirred at room temperature and a filtered solution of sodium 2-ethylhexanoate (9.13 g) in industrial methylated spirit (95% ethanol) (200 ml) was added over a period of 5 minutes to give a clear solution of pH 7.4. This solution was stirred slowly for 2 hours and the resulting crystalline suspension was stored at 0° for 20 hours. The product was collected by filtration, washed with industrial methylated spirit (5×25 ml) and dried at 40° in vacuo to give the required Form A sodium salt (17.7 g). The infrared spectrum (Nujol) resembles the reference.

EXAMPLE 3

Sodium (6R,7R)-3-acetoxymethyl-7-[(Z)-2-(fur-2-yl)-2-methoxyiminoacetamido]ceph-3-em-4-carboxylate, Form B, (4.4% m/m H$_2$O) (2.0 g) was stirred in industrial methylated spirit (95% ethanol) (30 ml) at room temperature for 1½ hours. The solid was collected by filtration, washed with industrial methylated spirit (4×5 ml) and dried at 40° in vacuo to produce the required Form A sodium salt (1.80 g). The infrared spectrum (Nujol) resembles the reference.

EXAMPLE 4

Sodium (6R,7R)-3-acetoxymethyl-7-[(Z)-2-(fur-2-yl)-2-methoxyiminoacetamido]ceph-3-em-4-carboxylate (containing some Form A) (60 g) was dissolved in water (60 ml) and industrial methylated spirit (95% ethanol) (60 ml). The solution was clarified by filtration and added to 1.2 l of industrial methylated spirit. The clear solution was seeded and stirred for 30 minutes at ambient temperature and then stored at 0° for 68 hours. The crystalline solid which precipitated out was collected by filtration, washed with industrial methylated spirit (4×50 ml) and dried at 40° in vacuo for 18 hours to give the required Form A sodium salt (41.55 g). The infrared spectrum (Nujol) resembles the reference.

EXAMPLE 5

Sodium (6R,7R)-3-acetoxymethyl-7-[(Z)-2-(fur-2-yl)-2-methoxyiminoacetamido]ceph-3-em-4-carboxylate (dioxan solvate) (3 g) was dissolved in water (3 ml) and industrial methylated spirit (95% ethanol) (3 ml). The solution was added to industrial methylated spirit (60 ml) and stirred for 30 minutes at ambient temperature. The crystalline suspension was stored at 0° for 3 hours and then the precipitated solid was collected by filtration, washed with industrial methylated spirit (4×3 ml) and dried at 30° in vacuo for 18 hours to produce the required Form A sodium salt (1.64 g). The infrared spectrum (Nujol) resembles the reference.

EXAMPLE 6

Sodium (6R,7R)-3-acetoxymethyl-7-[(Z)-2-(fur-2-yl)-2-methoxyiminoacetamido]ceph-3-em-4-carboxylate (dioxan solvate) (20 g) was dissolved in water (20 ml) and industrial methylated spirit (95% ethanol) (40 ml). The solution was stirred with charcoal (1 g) for 15 minutes and filtered through Kieselguhr, and the filtration bed was washed with a mixture of industrial methylated spirit (30 ml) and water (1 ml). The clear filtrate was stirred and industrial methylated spirit (350 ml) was added. The solution was seeded and stirred for 15 minutes and stored at 0° for 20 hours. The resulting crystalline product was collected by filtration, washed with industrial methylated spirit (4×10 ml) and dried at 40° in vacuo for 18 hours to give the required Form A sodium salt (8.45 g). The infrared spectrum (Nujol) resembles the reference.

A second crop (4.95 g) was obtained by concentration of the liquors.

EXAMPLE 7

Sodium (6R,7R)-3-acetoxymethyl-7-[(Z)-2-(fur-2-yl)-2-methoxyiminoacetamido]ceph-3-em-4-carboxylate, Form B, (4.4% m/m H$_2$O) (2.0 g) was dissolved in a mixture of water (2 ml) and industrial methylated spirit (95% ethanol) (4 ml). The solution was stirred and industrial methylated spirit (96 ml) was added rapidly. The clear solution was stored at 0° for 18 hours and the crystalline product collected by filtration, washed with industrial methylated spirit (4×3 ml) and dried at 40° to produce the required Form A sodium salt (1.30 g). The infrared spectrum (Nujol) resembles the reference.

EXAMPLE 8

Sodium (6R,7R)-3-acetoxymethyl-7-[(Z)-2-(fur-2-yl)-2-methoxyiminoacetamido]ceph-3-em-4-carboxylate, Form B, (4.4% m/m H$_2$O) (1.0 g) was dissolved in methanol (12.5 ml) at 40°. Industrial methylated spirit (95% ethanol) (25 ml) was added and the clear solution stood at 0° for 18 hours. The crystalline product was collected by filtration, washed with industrial methylated spirit (4×2 ml) and dried at 40° in vacuo to give the required Form A sodium salt (0.10 g). The infrared spectrum (Nujol) resembles the reference.

EXAMPLE 9

A solution of (6R,7R)-3-acetoxymethyl-7-[(Z)-2-(fur-2-yl)-2-methoxyiminoacetamido]ceph-3-em-4-carboxylic acid (ca. 21 g) in dichloromethane (215 ml) and dimethylacetamide (15 ml) was evaporated under reduced pressure and the residue was dissolved in industrial methylated spirit (150 ml). The solution was stirred with charcoal (2 g) for 30 minutes, filtered through kieselguhr, and the bed was washed with industrial methylated spirit (50 ml). The filtrate was stirred and a filtered solution of sodium 2-ethylhexanoate (9.13 g) in industrial methylated spirit (200 ml) was added. The resulting solution was seeded and stirred at ambient temperature for 16 hours. The product was collected by filtration, washed with industrial methylated spirit (5×25 ml) and dried at 40° in vacuo to give the required Form A sodium salt (18.96 g). The infrared spectrum (Nujol) resembles the reference.

EXAMPLE A

Dry Powder for Injection

The sterile Form A sodium (6R,7R)-3-acetoxymethyl-7-[(Z)-2-(fur-2-yl)-2-methoxyiminoacetamido]ceph-3-em-4-carboxylate is filled into glass vials, the contents of each container being equivalent to 500 mg and 1.00 g of the cephalosporin free acid. Filling is carried out aseptically under a blanket of nitrogen. The vials are closed using rubber discs or plugs held in position by aluminum sealing rings, thereby preventing a gaseous exchange or ingress of microorganisms. The product is intended for reconstitution with Water for Injections or other suitable sterile vehicle shortly before administration.

EXAMPLE B

| Intramammary Injection (Veterinary) | |
| --- | --- |
| Form A sodium (6R,7R)-3-acetoxymethyl-7-[(Z)-2-(fur-2-yl)-2-methoxyimino-acetamido]ceph-3-em-4-carboxylate. | 150mg |
| Polysorbate 60 3.0% w/w | |
| White Beeswax 6.0% w/w | to 3.00g |
| Arachis Oil 91.0% w/w | |

The last three ingredients are heated together at 150° C. for one hour and then cooled to room temperature with stirring. The sterile, milled antibiotic is added aseptically to this vehicle and refined with a high speed mixer. The product is filled aseptically into sterile plastic syringes, using a fill weight of 3.00 g per container.

EXAMPLE C

Injection for Veterinary Use

| | |
|---|---|
| Form A sodium (6R,7R)-3-acetoxymethyl-7-[(Z)-2-(fur-2-yl)-2-methoxyimino-acetamido]ceph-3-em-4-carboxylate. | 15.0% w/v |
| Aluminium Distearate 1.5% w/v | } to 100.0% w/v |
| Ethyl Oleate to 100% w/v | |

The aluminum distearate is dispersed in ethyl oleate, then heated at 150° for one hour with stirring and cooled to room temperature. The sterile, milled antibiotic is added aseptically to the vehicle and refined with a high speed mixer. The product is filled aseptically into injection vials and closed with rubber seals or plugs held in position by aluminum overseals.

I claim:

1. A sodium salt of (6R,7R)-3-acetoxymethyl-7-[(Z)-2-(fur-2-yl)-2-methoxyiminoacetamido]ceph-3-em-4-carboxylic acid containing less than 1% m/m of water and being non-hygroscopic at relative humidities within the range 25–83%.

2. A sodium salt of (6R,7R)-3-acetoxymethyl-7-[(Z)-2-(fur-2-yl)-2-methoxyiminoacetamido]ceph-3-em-4-carboxylic acid which substantially exhibits the following 'd' values and relative intensities when subjected to Debye Scherrer powder X-ray diffraction in a 114.6 mm diameter camera using Co Kα radiation:

| 'd' Value (Å) | Relative Intensity (I/I$_{100}$) |
|---|---|
| 14.4 | 55 |
| 12.3 | 100 |
| 9.9 | 45 |
| 7.16 | 36 |
| 6.79 | 64 |
| 6.59 | 73 |
| 6.35 | 9 |
| 6.11 | 5 |
| 4.92 | 27 |
| 4.69 | 100 |
| 4.49 | 41 |
| 4.20 | 9 |
| 4.00 | 45 |
| 3.91 | 36 |
| 3.78 | 36 |
| 3.64 | 90 |
| 3.55 | 36 |
| 3.36 | 18 |
| 3.30 | 27 |
| 3.25 | 9 |
| 3.16 | 18 |
| 3.08 | 27 |
| 2.86 | 18 |
| 2.81 | 18 |
| 2.76 | 14 |
| 2.60 | 14 |
| 2.56 | 4 |
| 2.45 | 18 |
| 2.42 | 14 |
| 2.36 | 4 |
| 2.31 | 18 |
| 2.262 | 14 |
| 2.188 | 23 |
| 2.054 | 9 |
| 2.025 | 4 |
| 2.000 | 4 |
| 1.915 | 4 |
| 1.800 | 2 |

-continued

| 'd' Value (Å) | Relative Intensity (I/I$_{100}$) |
|---|---|
| 1.728 | 2 | and/or the infra-red spectrum as a Nujol mull shown in the accompanying drawing.

3. A process for the preparation of the sodium salt of (6R,7R)-3-acetoxymethyl-7-[(Z)-2-(fur-2-yl)-2-methoxyiminoacetamido]ceph-3-em-4-carboxylic acid as claimed in claim 1 which comprises crystallising the said salt from a solution of a sodium salt of (6R,7R)-3-acetoxymethyl-7-[(Z)-2-(fur-2-yl)-2-methoxyiminoacetamido]ceph-3-em-4-carboxylic acid or a solvate thereof in an ethanolic solvent medium containing not greater than about 6% by volume of water.

4. A process as claimed in claim 3 wherein the starting sodium salt or solvate thereof is slurried with industrial methylated spirit whereby the desired sodium salt crystallises.

5. A process as claimed in claim 3 wherein the starting sodium salt or solvate thereof is first dissolved in an aqueous industrial methylated spirit containing 25 to 50% by volume of water and the desired sodium salt is caused to crystallise therefrom by diluting the solution with industrial methylated spirit containing not more than 1% by volume of water until the water concentration is not greater than about 6% by volume.

6. A process as claimed in claim 3 wherein the starting sodium salt is first formed in situ.

7. A process as claimed in claim 6 wherein a solution of (6R,7R)-3-acetoxymethyl-7-[(Z)-2-(fur-2-yl)-2-methoxy-iminoacetamido]ceph-3-em-4-carboxylic acid in an organic solvent optionally containing water, is treated with a solution of a sodium salt of an organic acid in industrial methylated spirit whereby the desired sodium salt crystallises.

8. A process as claimed in claim 6 wherein a solution of (6R,7R)-3-acetoxymethyl-7-[(Z)-2-(fur-2-yl)-2-methoxy-iminoacetamido]ceph-3-em-4-carboxylic acid in an organic solvent optionally containing water is extracted with an aqueous solution of a sodium salt of a weak organic acid and the aqueous extract is thereafter diluted with industrial methylated spirit until the water content of the resulting solution is not greater than about 6% by volume, whereupon the desired sodium salt crystallises.

9. A process for the preparation of the sodium salt of (6R,7R)-3-acetoxymethyl-7-[(Z)-2-(fur-2-yl)-2-methoxyiminoacetamido]ceph-3-em-4-carboxylic acid as claimed in claim 1 which comprises forming sodium (6R,7R)-3-acetoxymethyl-7-[(Z)-2-(fur-2-yl)-2-methoxyiminoacetamido]ceph-3-em-4-carboxylate in solution from (6R,7R)-3-acetoxymethyl-7-[(Z)-2-(fur-2-yl)-2-methoxyimino acetamido]ceph-3-em-4-carboxylic acid and crystallising the desired sodium salt from an ethanolic medium containing not greater than 6% by volume of water.

10. A pharmaceutical composition comprising the sodium salt as claimed in claim 1 adapted for use in human medicine.

11. A pharmaceutical composition comprising the sodium salt as claimed in claim 1 adapted for use in veterinary medicine.

12. A method of combatting a bacterial infection in an animal which comprises administering to said animal a therapeutically effective amount of the sodium salt claimed in claim 1.

* * * * *